United States Patent [19]

Hoogendijk

[11] Patent Number: 5,312,528

[45] Date of Patent: May 17, 1994

[54] METHOD OF DETERMINING, WITH THE AID OF AN ION-SELECTIVE ELECTRODE, THE CONCENTRATION OF A SUBSTANCE TO BE DETERMINED, AND APPARATUS TO BE USED IN SAID METHOD

[75] Inventor: Robert Hoogendijk, Spijkernisse, Netherlands

[73] Assignee: Applikon Dependable Instruments B.V., Schiedam, Netherlands

[21] Appl. No.: 894,112

[22] Filed: Jun. 5, 1992

[30] Foreign Application Priority Data

Jun. 7, 1991 [NL] Netherlands ............... 9100984

[51] Int. Cl.$^5$ ............................. G01N 27/26
[52] U.S. Cl. .................... 204/153.21; 204/153.23; 204/153.1; 204/405; 204/433; 204/435
[58] Field of Search ............... 204/405, 416, 153.23, 204/153.1, 433, 435, 153.21

[56] References Cited

U.S. PATENT DOCUMENTS

| | | | |
|---|---|---|---|
| 3,730,685 | 5/1973 | Prohaska | 204/405 |
| 3,738,812 | 6/1973 | Berry et al. | 204/405 |
| 5,174,872 | 12/1992 | Scott | 204/416 |

OTHER PUBLICATIONS

The Analyst, vol. 103, No. 1225, Apr. 1, 1978, Automatic Titration by Stepwise Addition of Equal Volumes of Titrant, pp. 305–316, By A. Johansson et al.

Dissertation Abstracts International Section B, vol. 50, No. 8, Feb. 1, 1990, by T. R. Berube, p. 3488.

Analytical Chemistry, vol. 51, No. 2, Feb. 1, 1979, Optimizing Precision in Standard Addition Measurement, pp. 232–235, by K. L. Ratzlaff.

Fresenius Zeitschrift Fur Analytische Chemie, vol. 325, 1986, pp. 263–266, Optimizing Precision in Standard Additions Determinations, by M. J. Gardner et al.

*Primary Examiner*—Kathryn Gorgos
*Assistant Examiner*—Bruce F. Bell
*Attorney, Agent, or Firm*—Bachman & LaPointe

[57] ABSTRACT

The invention relates to a method of determining an ion concentration with the aid of an ion-selective electrode, in which method a known quantity by volume of a sample is taken, a buffer is added and the initial potential of the electrode pair is measured, a known volume having an accurately known ion concentration is added and the potential obtained is measured, the standard solution being added stepwise, and the initial potential of the electrode pair and the slope of the relationship between potential and logarithm of the concentration is calculated for each of the quantities added from the data obtained, a small quantity of the solution to be determined is added, the potential difference is measured and the latter is compared with the required sudden change in potential, after which a sample is again taken and a quantity of the solution to be determined is added which is expected to bring the sudden change in potential into the required region, the potential is then read off and the required concentration is calculated. A description is furthermore given of an apparatus which is suitable for performing said method.

13 Claims, 3 Drawing Sheets

METHOD OF DETERMINING, WITH THE AID OF AN ION-SELECTIVE ELECTRODE, THE CONCENTRATION OF A SUBSTANCE TO BE DETERMINED, AND APPARATUS TO BE USED IN SAID METHOD

The invention relates to a method of determining, with the aid of an ion-selective electrode (ISE), the concentration of a substance to be determined, in which method a known volume of a sample is taken and, if necessary, the latter is diluted to bring it within the detection range of the ISE, a buffer is added to the solution in order to produce a medium in which the potential of the ISE is directly related to the concentration of the respective ion and, after a set reaction time, the initial potential of the electrode pair (ion-selective electrode and reference electrode) is measured, then a known volume having an accurately known ion concentration (standard solution) is added and the change in potential produced is measured, and the concentration of the substance to be determined is calculated therefrom.

Such a method is disclosed in Analytical Chemistry, 51, No. 2, February 1979, pages 232-235. The paper provides equations and graphs which describe the effect of the increment size on the precision of a standard addition or standard subtraction measurement.

Fresenius, Z. Anal. Chem. (1986), 325, pages 263-266 describes the improvement of the precis-,on in determinations carried out by a standard addition method. In its simplest form, such a method comprises the measurement of the sample, followed by an addition of a known quantity of substance to be determined, followed by a second determination. The original concentration of substance to be determined is then obtained by plotting the results on a graph or is calculated from the increase in the signal produced by the addition. After that, still further additions may be made. To obtain good results by the standard addition method, it is necessary for the response of the analytical method adopted to be linear, or to be capable of being rendered linear, for a concentration of substance to be determined ranging from zero to the sum of the highest sample concentration and the largest addition. The interference must have a constant relationship to the concentration of substance to be determined. Finally, the response to the analytical method must be the same for every added substance to be determined as for the substance to be determined originally present in the sample.

The Analyst, Vol. 103, No. 1225 dated April 1978, pages 305 to 316 discloses that potentiometric titrations in which the titration curve is plotted or the titration curve is interrupted at a predetermined end point have important disadvantages. To obtain satisfactory results, a) the reaction between titrant and solution to be titrated must proceed rapidly, b) the response time of the indicator electrode must be short and c) the electrode potentials at the equivalence point must be stable and reproducible. To overcome these disadvantages, the titrant is added stepwise. In this case, equivalence volumes are not read off but calculated.

In these known methods, better results can be obtained by a correct choice of the standard addition volume, that is to say large enough to produce a readily measurable potential difference and small enough to be of the order of magnitude of the first potential in order to ensure that the same measurement range of the electrode is used. In the standard addition method, therefore, the volume must be dependent on the sample concentration to be expected. In this method, it is also necessary to determine the slope of the electrode system, specifically before the analysis. Said slope is determined using the same method but with a standard concentration instead of with a sample. Obviously, the slope must be determined in the same range as the concentration of the sample.

A method of the type described at the outset has now been found which makes it possible to automate the determination. Said method is characterised in that the addition of the standard solution to the reaction mixture is carried out in steps, the first addition being a small one which brings about a change in potential indicating what the concentration of the substance to be determined is approximately, then further additions are made on the basis of the change in potential produced until the final change in potential is such that it is large enough to be able to measure accurately and not so large that it falls outside the respective calibration region. As a result of determining not only a slope, but, as it were, dividing the range into a number of fragments and always determining the slope thereof, a better accuracy is achieved and the effect of a nonlinear relationship on the calculations is also suppressed.

Characteristic of this method is that the introduction of a sample and the addition of the standard solution is performed in steps, the slope of the potential with respect to the logarithm of the concentration being calculated for each step and further processed in the known manner on the basis of these data obtained.

In performing the method in practice, the electrode system will first be calibrated. This is done by introducing a known volume of a blank (the same as the sample) into the reaction cell and adding a known volume of buffer solution. Depending on the set program of the system, a number of measurement ranges may be calibrated, i.e. the slope can be determined in that range. These intervals cover a maximum of two decades taken together within the concentration range from 0.1 to 10% of the standard concentration. A further dilution of the sample as a result of standard addition of 0.1 is usually undesirable and 0.1 of the sample volume is usually still large enough to still dose accurately with the appropriate equipment.

If one slope is determined, directly after the addition of the buffer, a volume unit of standard solution is added which forms, for example, 1% of the sample volume. In measuring the potential of the electrodes, a 10-fold increase in concentration (1 decade) is achieved by adding a certain volume of standard solution (approximately 10%), the dilution factors which are achieved by adding the standard itself being included in the calculation. The potential measurements are performed on the basis of a drift criterion, that is to say, the potential is measured when the electrode potential shift produced by the standard additions has reached the programmed shift.

If a plurality cf slopes has to be measured, the first standard volume addition will be 0.1% of the sample volume. The slopes are then determined by adding the subsequent standard solution volumes which result in the required increase in concentration, allowance being made for the dilution. To determine four slopes, for example, five standard additions are necessary.

The electrode system can be calibrated by introducing a known volume of a blank into the reaction cell, adding a known volume of buffer solution and then adding the standard solution stepwise, the quantity added in a standard solution being fractions of the blank volume, and calculating the slopes of the relationship between the potential of the electrode pair and the logarithm of the concentration for each of the measurement ranges produced by the addition from the changes in potential produced, the response time of the electrode pair also being determined in each measurement range.

After the calibration, the analysis is performed. To do this, a small quantity of standard solution is first added to indicate the concentration of the sample of the substance to be determined, which does not exceed 10 times the minimum concentration encountered in said sample or optionally diluted sample.

In particular, the quantity of standard solution added in this connection does not exceed 3 times the minimum concentration encountered.

In the addition of the standard solution to determine the concentration of substance in the sample, a final change in potential is aimed at which corresponds to an increase in the concentration of 1.5 to 10 times, in particular 3 to 5 times the concentration of the substance to be determined which was present in the sample or the optionally diluted sample.

Advantageously, the number of quantities of standard solutions with which the various measurement ranges are calibrated are chosen in such a way that more and smaller ranges are obtained in that section of the response characteristic of the ISE where it is nonlinear.

Another advantageous embodiment comprises the correction of the potential of the ISE for the effect of temperature with the aid of a temperature sensor.

The invention also relates to an apparatus suitable for performing the method according to the invention. Said apparatus is characterised by a mixing vessel provided an ion-selective electrode and a reference electrode, which may be combined if desired, a stirring device, an inlet for a sample, a pump which pumps a quantity of sample to the determination vessel via a sampling pipe, which mixing vessel is connected to a motor-controlled burette which is measured or controlled by a microprocessor system which can be operated by means of a keyboard and display, and an inlet for a standard liquid, buffer solution and blank liquid, and which mixing vessel is also provided with a rinsing device for rinsing and a microprocessor for the purpose of calculation and of controlling the apparatus, the measured voltage of the potential being amplified to reach a region which can be processed by the processor, being converted in an a/d convertor and being fed to the microprocessor, which microprocessor is provided with an input facility for data and is connected to the indicator and to a programming unit, a read-out function also being available. Advantageously, a temperature sensor is also present.

In the method according to the invention it is possible not always to wait after each standard solution addition until the potential of the ISE has reached a stable signal, but to estimate the final potential on the basis of the initial change in potential after a fresh addition. Advantageously, this estimate is made on the basis of the response time of the ISE which has been determined in each calibration range when the ISE was determined.

After the last addition of the standard solution, it is advantageous to delay the determination of the ISE potential until it fulfils a particular test criterion.

According to another advantageous embodiment, the fractions of the blank volume added to the standard solution are such that the change in concentration produced is not less than 1.5 times the previous concentration and not greater than 10 times said concentration, with the first addition being excepted.

In the method according to the invention, a large amount of computational work may be required, and use is advantageously made of modern electrical engineering involving a microprocessor and a memory in said computational work and in setting measured data and in storing calibration data obtained.

As a result of using the method according to the invention together with the microprocessor, an automated determination with high accuracy is possible.

Figure 1:
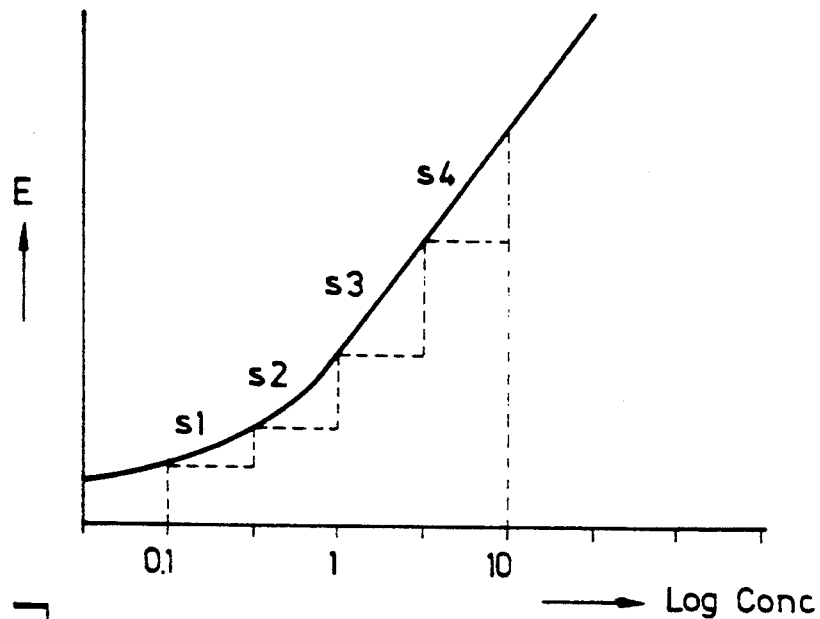
FIG. 1 illustrates four slopes of a half decade each.

The analysis system to be used according to the invention consists of an automated sampling device, which may be either a sampling device which takes the samples from a process flow or another type of sample exchanger. The system furthermore comprises a measuring compartment containing a reaction cell into which the sample is introduced and in which the electrodes are placed. Buffer and standard solution are added to the reaction cell with the aid of a precision dosing device such as, for example, a motor-driven burette. The reaction cell is constructed in such a way that it can be rinsed and emptied between the various analyses, this being done, for example, with the aid of valves or pumps. The system also comprises a stirring device for mixing the solution in the reaction cell during an analysis.

All the components are preferably regulated by a microprocessor system which performs a timing program. The electrode potentials are measured with the aid of a high-impedance amplifier, after which the signal can be processed further and can be converted by an a/d convertor. The converted signal is then also processed by the microprocessor.

The course of events in the dynamic standard addition method, the method according to the invention, is the same, in basic principle, as the conventional method, but the problems caused by a considerable variation in ion concentration are now controlled. In performing the method with the system described above it will be clear that this is not in principle a suitable way of approximately knowing the ion concentration in the sample for choosing the best calibration range and the best addition volume.

Choosing the initial potential of the electrodes (when a standard addition has not yet been made) would be one possibility. However, this is not very reliable since the potential of the electrode may drift or vary with time. This is mainly due to aging and contamination of the membrane of the electrode. Moreover, the potential value is absolutely unreliable as a result of the matrix effects in the sample. In the method according to the invention, this can be overcome by the calibration. The calibration is performed as follows.

A known volume of a blank (the same as the sample) is introduced into the reaction cell and a known volume of buffer solution is added. Depending on the set program (which, in the case of completely automated equipment, can be set) a number of measurement ranges are calibrated, that is to say the slope of said range can be determined. These intervals may cover at most two decades within the concentration range of 0.1 to 10% of the standard concentration. These percentages result from the fact that a further dilution of the sample as a result of the standard addition volume of 0.1 (i.e. 10% of the sample volume) is usually undesirable and 0.1% of the sample volume is usually large enough for accurate addition with a precision addition device.

In this connection, the following subdivisions may be used.

A slope over one decade.
Two slopes over one decade each.
Three slopes, two over a half decade, one over one decade.
Four slopes of a half decade each.

FIG. 1 illustrates this last choice. The calibration range in this figure is 0.1 to 10 ppm. A 0.1 ppm concentration is achieved, for example, by adding a volume, equivalent to 0.1% of the sample volume, of a 100 ppm standard to said sample.

In the case where one slope is determined, immediately after the addition of the buffer, a volume of standard solution is added which, is equal to 1% of the sample volume. In measuring the potential of the electrode, a 10-fold increase in concentration is achieved (one decade) by adding a certain volume of a standard solution (approximately 10%), allowance being made for the dilution factors which are produced as a result of adding the standard itself (see calculations). The potential measurements are performed on the basis of a drift criterion, i.e. the potential is measured when an electrode potential drift resulting from the standard additions has reached the programmed drift.

If a plurality of slopes have to be determined, the first standard volume to be added will be 0.1% of the sample volume. The slopes are then determined by adding the subsequent volumes of the standard solution which result in the required increase in concentration, allowance again being made for the dilution aspects. To determine four slopes, for example, five standard additions are required.

In this method, the problems with nonlinear response of the electrode which occur, in particular, in the low or fairly high measurement region of the electrode, are overcome. In this connection it is pointed out that nonlinearity of the electrode increases with ageing.

The analysis is performed as follows.

A known volume of a sample is introduced into the reaction cell and a known quantity of buffer is then added. When the drift criterion is fulfilled, the initial potential is measured. Then the suitable addition volume is added.

To determine the appropriate volume, a test volume is added which would be the appropriate addition volume (as is explained below) if the concentration of the sample were the same as the lowest point in the calibration range; 0.1% of the standard addition. This test volume is 0.316% of the sample volume, corresponding to half a decade.

After the drift criterion signal is stable, the electrode potential is measured again. The difference between the initial and the "test" potential is now assessed to determine the range corresponding to the concentration of the sample. When an indication is obtained, an addition can be chosen which is such that the possible difference in potential after the addition is approximately half the value of the slope, that is to say 30 mV if the slope of the electrode is approximately 59 mV/decade at 20° C. This potential difference is deemed to be the optimum addition for performing accurate measurements. The object of this procedure is to calculate a potential difference which is within one third to two thirds of the slope calculated in mV. The following table can be used to choose the appropriate addition for an electrode having a slope of approximately 59 mV/decade.

| | | | |
|---|---|---|---|
| 1 | $\Delta E_{ind} >$ | 30 mV: | finished, concentration calculated |
| 2 | $\Delta E_{ind} >$ | 10 mV: | calculate a further addition |
| 3 | $\Delta E_{ind} >$ | 4 mV: | metered addition of 1% of the sample volume |
| 4 | $\Delta E_{ind} >$ | 1.5 mV: | metered addition of 3.16% of the sample volume |
| 5 | $\Delta E_{ind} <$ | 1.5 mV: | metered addition of 10% of the sample volume |

In Case 1, the sample concentration was in the lowest region of the calibration and the desired potential difference has already been achieved.

In Case 2, the "test" addition requires an adjustment to achieve the potential difference of 30 mV. This adjustment is made by a further standard addition, which can easily be calculated from the initial standard addition and the potential difference produced thereby (see the calculations).

In Case 3, 4 and 5, it is assumed that the sample concentration corresponds to the subsequent decade or to the last half decade or higher, respectively. The potential differences produced by these additions are remeasured. If the potential difference does not exceed 30 mV, an adjustment is again made, as a result of which a further addition is carried out which can be calculated in the two ways described.

In certain cases, the sample concentration may exceed the calibration range. In that case, it may be desirable not to make a standard addition which results in a potential difference of 30 mV. This is intended to avoid an excessive consumption of standard solution. If the sample concentration exceeds to the concentration of the standard solution, an addition is not even possible because addition will cause standard dilution of the sample instead of increasing the concentration. If the 30 mV potential difference can not be achieved within a reasonable quantity of standard solution (for example the contents of 1 burette), the method can be performed with a smaller addition than the optimum one, accuracy being sacrificed to some extent.

Finally, the sample concentration is calculated from the measured potential difference and the sum of the standard additions. In this calculation, the slope associated with the calibration range in which measurement is carried out is used. It is possible for the measurements to comprise two ranges, in which case weighted average of the slopes is used in the calculation. If the measurement range falls outside the calibration range, the highest or lowest slope of the calibration range is used.

The calculations are explained below.

Calculation

E = electrode potential
S = slope of the electrode
Cs = concentration in the sample
Ca = concentration of the standard solution
Vs = sample volume
Vo = sample + buffer volume
Va = addition volume
Nernst's law: $E = RT/nF \cdot \log [C]$
R = gas constant, T = temperature, $RT/nF = s$
n = valency of ion, F = Faraday constant
$E = s \cdot \log [C]$  (1)

CALCULATION OF THE ION CONCENTRATION IN THE SAMPLE initial potential before the addition: $Eo = s \cdot \log [Cs]$
potential after the standard addition:

$$Ea = s \cdot \log \left[ Ca \cdot \frac{Va}{(Vo + Va)} + Cs \cdot \frac{Vo}{(Vo + Va)} \right]$$

potential difference:

$$Ea - Eo = s \cdot \log \left[ \frac{Ca}{Cs} \cdot \frac{Va}{(Vo + Va)} + \frac{Vo}{(Vo + Va)} \right]$$

after correction for dilution of the sample by the buffer volume, the sample concentratio is:

$$Cs = \frac{Ca}{\frac{(Vo + Va)}{Va} \cdot 10^{\Delta E/s} - \frac{Vo}{Va}} \cdot \frac{Vo}{Vs} \quad (2);$$

$$\text{dilution factor} = \frac{Vo}{Vs}$$

CALCULATION OF THE SUBSEQUENT VOLUME OF THE STANDARD SOLUTION IN THE CALIBRATION PROCEDURE

In the calibration, the subsequent additions of standard are made to a blank solution to create a certain concentration step. The change in potential is used to calculate the slope of the electrode in that range. The concentration step is shown in the following equation as X. The value of X, for example may be 10, that is to say precisely 1 decade in a concentration change. Vf and Vn indicate, respectively, the previous addition volume (which may be the sum of all the additions to that point) and the subsequent addition to achieve an X-fold increase in concentration:

$$\frac{Vf}{Vo + Vf} \cdot X = \frac{Vf + Vn}{Vo + Vf + Vn}$$

From this equation, Vn can readily be calculated:

$$Vn = \frac{(X - 1) \cdot Vf \cdot (Vo + Vf)}{(Vo + Vf) - X \cdot Vf} \quad (3)$$

CALCULATION OF THE FURTHER ADDITION REQUIRED TO ACHIEVE A POTENTIAL DIFFERENCE OF APPROXIMATELY ½ S

In this situation, a volume of standard solution (Va) is added which results in a potential difference of $\Delta V$, and $\Delta E$ is less than ½ s. A further addition (Ve) is required to set the potential difference to ½ s, so that the total volume added becomes:

$$Vt = Va + Ve$$

From the first addition of the total addition, the sample concentration can be calculated using Equation 2:

$$Cs = \frac{Ca}{\frac{(Vo + Va)}{Va} \cdot 10^{\Delta E/s} - \frac{Vo}{Va}} = \quad (4)$$

$$\frac{Ca}{\frac{(Vo + Vt)}{Vt} \cdot 10^{\frac{1}{2}s/s} - \frac{Vo}{Vt}}$$

$$\frac{(Vo + Vn)}{Va} \cdot 10^{\Delta E/s} - \frac{Vo}{Va} = \frac{(Vo + Vt)}{Vt} \cdot 10^{\frac{1}{2}} - \frac{Vo}{Vt}$$

Isolate Vt and rearrange:

$$Vt = \frac{Vo \cdot Va \cdot (10^{\frac{1}{2}} - 1)}{Vo \cdot (10^{\Delta E/s} - 1) + Va \cdot (10^{\Delta E/s} - 10)} \quad (5)$$

and, $Ve = Vt - Va$.

CALCULATION OF THE LIMIT OF THE POTENTIAL DIFFERENCE IN ORDER TO CHOOSE THE APPROPRIATE STANDARD ADDITION VOLUME.

To determine the potential difference limits, which dictate the concentration region corresponding to the sample concentration, Equation (4) is again used and the term $10^{\Delta E/s}$ is isolated from it:

$$10^{\Delta E/s} = \frac{Va}{(Vo + Va)} * \left( \frac{(Vo + Vt)}{Vt} * 3.16 - \frac{Vo}{Vt} + \frac{Vo}{Va} \right)$$

and assuming that Vo is appreciably larger than Vt and Va:

$$Vo \approx Vo + Va \approx + Vt$$

Substituting this and rewriting the last equation yields:

$$10^{\Delta E/s} = 2.16 \, Va/Vt + 1 \text{ and therefore: } \Delta E = s \cdot \log [2.16 \, Va/Vt + 1] \quad (6)$$

The potential differences can now be calculated from the formula (6) as a function of Vt, Va being known since this is the test volume of 0.316% of the sample volume. If the table is again used (the electrode therefore has a slope of approximately 59 mV/decade at 20° C.), the following limits are obtained, for the first limit volume of 1% is selected being the maximum further addition which is possible with the first try out volume.

| second addition % Vs | Vt in % Vs | ΔE limit mV |
| --- | --- | --- |
| 1% | 1.316% | 10.7 |
| 3.16% | 3.48% | 4.6 |
| 10% | 10.32% | 1.64 |

Usually a standard addition method comprises only one standard addition, but the present method can comprise up to three additions. The try out addition, a second addition based on the result of the test addition and an adjustment addition for the second addition. Consequently, a longer analysis time might be required. This effect can be overcome by the following measures.

Working with a time constant.

Figure 2:
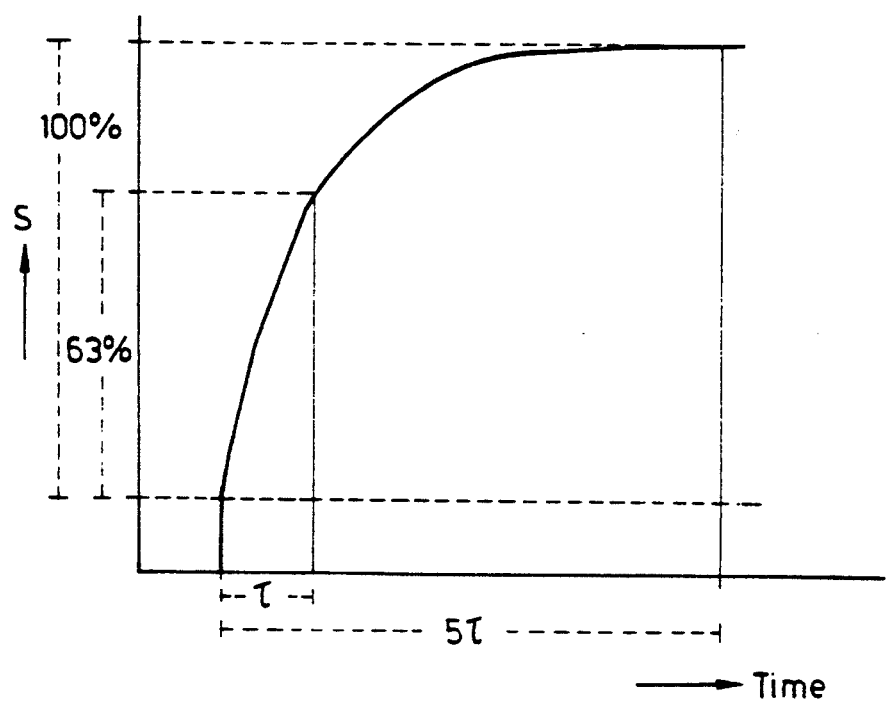
FIG. 2 illustrates the estimated potential difference which results from a second addition.

If a second addition is made, the results can be measured when the electrode signal is stable, but this requires a certain amount of time which is dependent on the electrode, the concentration region and the total volume. To shorten this time, the change in signal can be measured after a time constant ($\gamma$). It is assumed that the electrode response is a "quasi first order" response, 63% of the total signal change having occurred after 1$\gamma$ has elapsed. To determine the 1$\gamma$-point, the first derivative of the signal change is calculated on-line from the measurements; the 1$\gamma$-point is where the first derivative is 63% of the maximum value. This first order function has a positive signal change: $F(t) = 1 - E^{-t/\gamma}$ (see FIG. 2).

The first derivative: $f(t) = 1/\gamma e^{-t/\gamma}$ and if $t = 0$: $f(0) = 1/\gamma$ and if $t = \gamma$: $f(\gamma) = 1/\gamma \times 0.63$ (see FIG. 2).

The value obtained in this way is divided by 0.63 in order to obtain an estimated potential difference which results from the second addition. On the basis of this potential, a possible further addition is calculated and added. The result of this last addition can only be measured when a signal has stabilised. The result of the first test addition is also measured in this way in order to make possible a more reliable choice of the second addition. The stabilisation of the test addition requires little time because the sample concentration is not low. If the sample concentration is low, on the other hand, a second addition is unnecessary, so that it is improbable that time-consuming measurements are necessary.

Yet a further optimisation can be achieved if the response characteristic of the electrode is investigated instead of assuming that the characteristic is a first order function. The investigation can be performed during the calibration of the electrode. If the slope values of the various ranges are determined, the point can also be determined at which the first derivative is 63% of the maximum value. In this case it can be calculated whether this point does in fact correspond to 63% of the signal value. The deviation from 63% can be processed in the calculation of the potential value which is obtained in the second standard addition. If the percentage of the total signal difference is, for example, 80%, the correction factor is 0.8 instead of 0.63. This factor may be different for all the calibration ranges.

MEASUREMENTS AT LOW CONCENTRATIONS

As already stated, with a very low sample concentration, the stabilisation time may be longer than usual. In addition, the determination of these low concentrations is less accurate since the extrapolation to that region using the slope of the lowest calibration range is unrealistic. To achieve an improvement in this respect, the following modification may be used:

The first operation after the buffer is added to the sample volume which has been transferred to the reaction cell is to add a quantity, equivalent to 0.1% of the sample volume, of the standard solution. This results in a concentration of a solution which is at least equal to the minimum concentration of the lowest calibration range, that is to say, in the case of a sample with an ion concentration 0. The effect of this addition is that the electrode signal no,,i enters the calibration range and the response of the electrode is sufficiently fast. The increase in concentration as a result of this addition is subtracted from the final result to obtain a correct answer. It is clear, however, that some loss in accuracy occurs in these measurements below the limit of calibration.

TEMPERATURE CORRECTION

The electrode signal is dependent not only on all the factors discussed, but also on the temperature, as is evident from Equation (1). In order to eliminate the variations resulting from temperature changes, the temperature of the solution may be kept constant and processed in the results obtained.

In the calibration procedure and in the measurement procedure, the electrode potentials are normalised to, for example, 20° C. and are then used in all the equations.

The normalisation to a particular temperature is performed as follows: $E_{20} = 293/T \times E_T$, where T is the measured temperature (in kelvin).

ALGORITHM

Before the program which contains the logarithms described below can be performed by an analysis apparatus based a microprocessor, the following data have to be entered:
 a) drift criterion,
 b) number of calibration ranges,
 c) sample volume in ml,
 d) buffer volume in nil,
 e) concentration of the standard solution,
 f) design factor for calculating the final results in a cell having a certain size,
 g) slope factor, that is to say, the value of "n" from the Nernst equation (1) (for example, −1 for a fluorine electrode).

CALIBRATION

1. Take a sample and add buffer in the programmed manner.

2. Add a first or subsequent standard solution using Equation (3), depending on the choice of the number of slopes.

If No. = 1: 2 metered additions; first = 1% of Vs, subsequent: X = 10

If No. = 2: 3 metered additions; first = 1% of Vs, subsequent: X = 10 and 100

If No. = 3: 4 metered additions; first = 0.1% of Vs, subsequent: X = 3.16, 10 and 100

If No. = 4: 5 metered additions; first = 0.1% of Vs, subsequent: X = 3.16, 10, 31.6, 100

3. Wait a short time for the electrode response, which corresponds, for example, to 15 sec.

4. Measure until the signal is within the drift criterion and store the last value.

5. If a fresh addition has to be made, return to step 2.

6. Calculate the value of the slope (s) by measuring the potential differences of the respective increases in concentration. Calculate the correction factors which have to be used in estimating a signal from the second addition in the analytical procedure.

ANALYSIS

1) Take a sample and add buffer in accordance with the programmed routine.
2) Add standard solution, 0.1% of Vs:Vo.
3) Wait a short time for the electrode response, for example 15 sec.
4) Measure until the signal is within the drift criterion and store the last value: $E_o$.
5) Add a test addition, equal to 0.316% of Vs, of the standard solution:V1.
Repeat 3 and 4:$E_{ind}$.
Calculate the potential difference $\Delta E$, the limits for the application of Equation (6) and the actual slopes.
8) If the potential difference
$\Delta E_{ind}$ is greater than limit 1, proceed to 14,
$\Delta E_{ind}$ is greater than limit 2, proceed to 12,
$\Delta E_{ind}$ is greater than limit 3, add 1% of Vs:V2
$\Delta E_{ind}$ is greater than limit 4, add 3.16% of Vs:V2
$\Delta E_{ind}$ is less than limit 4, add 10% of Vs:V2.
Add 1% of Vs:V2.
Add 3.16% of Vs:V2.
Add 10% of Vs:V2.
9) Repeat 3
10) Measure the signal and determine the maximum value of the first derivative.
11) Measure the signal, if the first derivative is less than or equal to 63% of the maximum first derivative then count $E = E_T$ factor, proceed to the following step.
12) Calculate and add the further addition in accordance with Equation (5):V3.
13) Repeat 4:Et.
14) Calculate the sample concentration with Equation (2) using $\Delta E = ET - Eo$, $Va = V1 + V2 + V3$, and the appropriate slope of the respective range for a weighted average of two ranges. Subtract the concentration resulting from the addition of Vo (also using Equation (2)).

Figure 3:
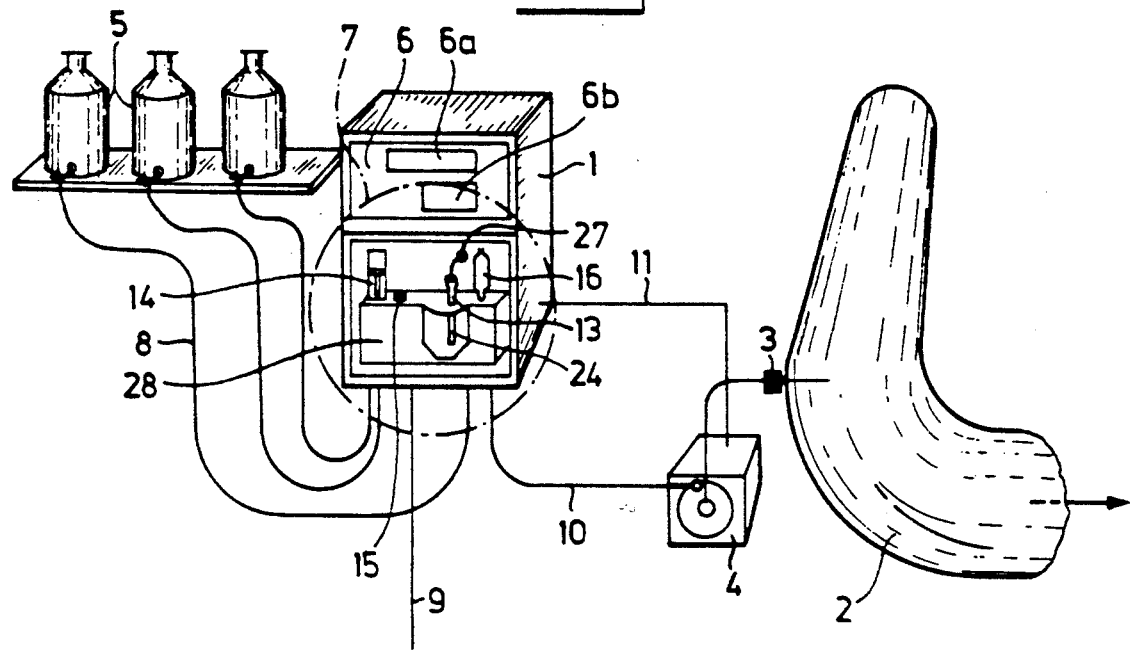
FIG. 3 shows a microprocessor controlled system according to the invention.
Figure 4:
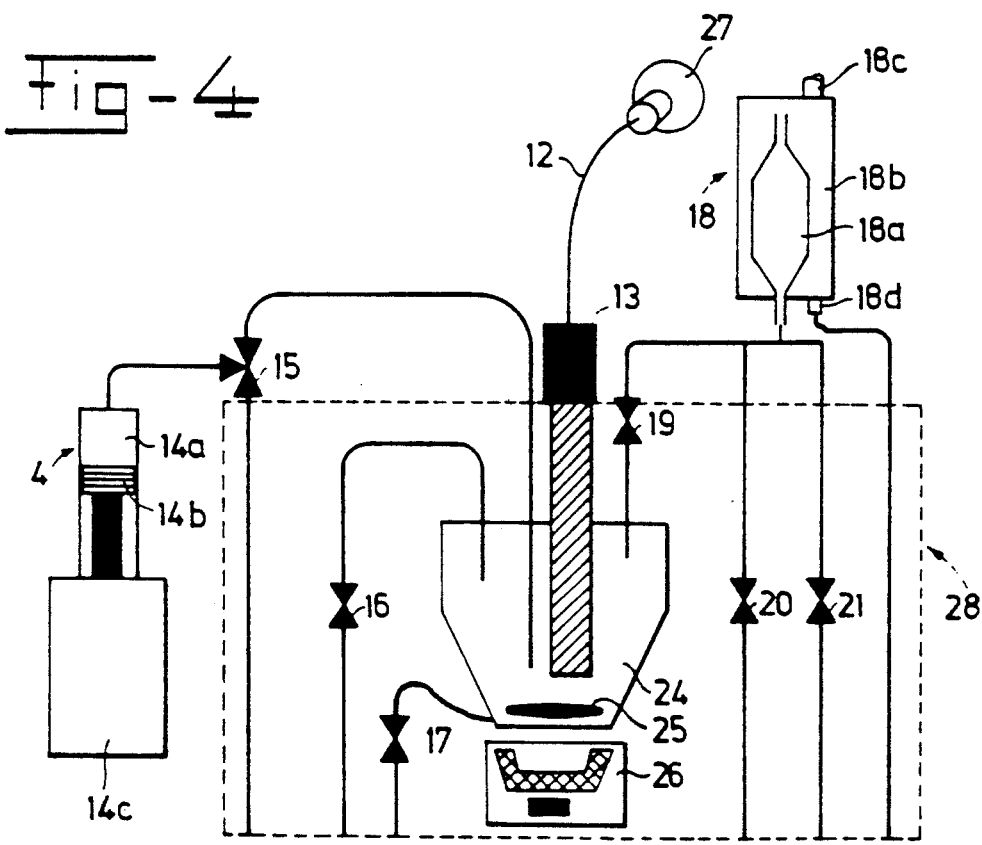
FIG. 4 shows a more detailed embodiment of the section of the analyzer which contains the ion selective electrode, valves, and micro-controlled burette.

The invention is explained below by reference to FIGS. 3, 4 and 5. These relate to a measurement in a process flow of a certain process from which a sample is taken and is fed to the analytical apparatus (1); this is also termed "on-line analysis".

One possibility for taking a sample from the process (represented here as a pipeline (2) is to make use of a pump (4) which pumps via a sampling pipe (3) a quantity of sample to the analyser via line (10). The pump is electronically activated by the analyser (1) via a control line (11). The analyser has a section in which the analysis is carried out (7) which is shown in more detail in FIG. 4. This section contains the ISE, various valves and a motor-controlled burette (14) which is measured or controlled by a microprocessor system in the analytical apparatus (see also FIG. 3). Said microprocessor system can be operated by means of a keyboard and display at the front of the analytical apparatus (6). To carry out the analysis by the standard addition method described here, use is made of various chemicals which are added to the sample in the reaction vessel (24). In this connection, a standard solution of the component to be measured, an ionic strength buffer solution and a blank liquid are normally involved. The blank liquid is used to calibrate the ISE. The various liquids are connected to the apparatus with the aid of hose material (8) and kept in containers (5). When the analysis has been carried out, the contents of the vessel are drained via line (9) and the procedure can then start again.

CONSTRUCTION OF THE ANALYTICAL SECTION

The actual analysis is performed in the wet section of the analytical apparatus (7). This is shown in FIG. 4. This section is constructed in such a way that all the electrical parts of the components are isolated in a waterproof manner from said wet section. The valves, the reaction vessel and the stirrer are together incorporated in a plastic block in order to produce a more compact design in this way. The analytical sequence is as follows:

The sample originating from the process is fed via valve (21) to the sample metering system (18) (consisting of pipette (18a)). The valve (21) and pump (4) remain on until the pipette (18a) contains a representative sample. The excess sample is taken up in the casing (18b) and drained via drain (18d). The system is vented via opening (18c). The next step in the procedure is to transfer the sample quantitatively to the reaction vessel (24). To do this, the valve (19) is opened. The vessel contains a stirring rod (25) which is set in motion via a rotating magnet (26). In this way, the sample is homogenised in the reaction vessel with an ionic strength buffer which is fed to the vessel via valve (16). The potential of the ISE (13), which now projects into the reaction mixture, can be measured. The ISE is connected to sensor input (27) via electrode cable (12). The modified standard addition method makes use of a standard solution which is metered in with the aid of a motor-controlled burette (14). This consists of a cylinder (14a) in which a piston moves (14b) which is driven by the motor (14c). An exact volume of standard solution can be added to the reaction mixture in vessel (24) via 3-way valve (15), after which the potential of the ISE at the new concentration can be measured. After completion of the analysis, the reaction mixture can be drained via valve (17). The cylinder can also be refilled via valve (15) if the latter is switched over.

DIAGRAMMATIC CONSTRUCTION OF ANALYTICAL APPARATUS

Figure 5:
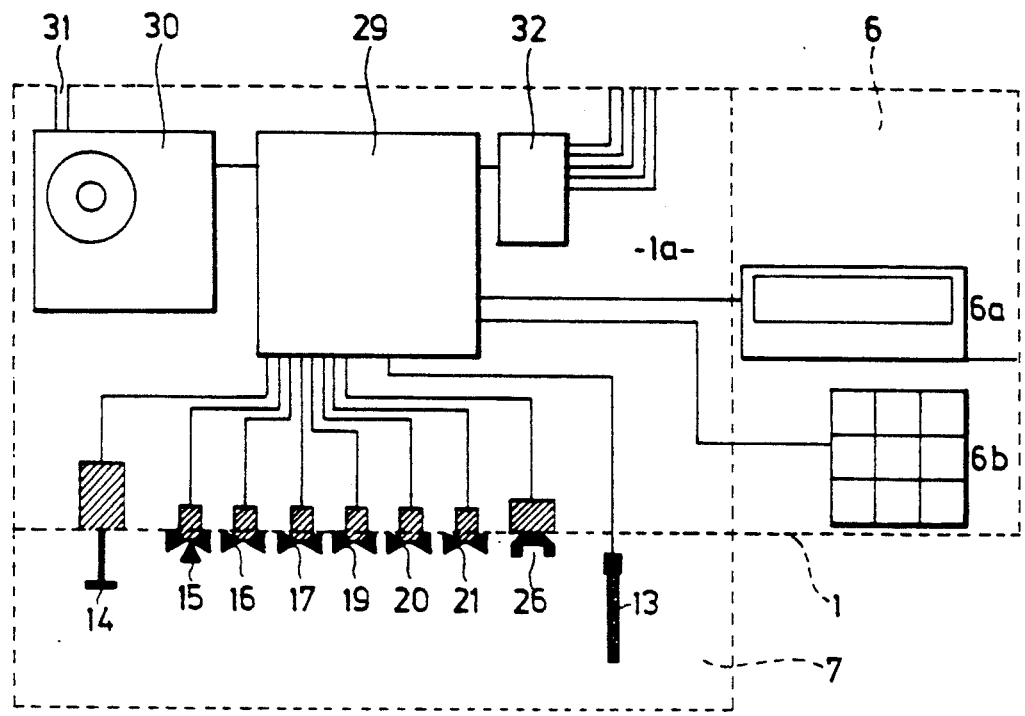
FIG. 5 shows the diagram of the analytical apparatus.

FIG. 5 shows the diagram of the analytical apparatus (1). The microprocessor board (29) is central to it; it contains all the necessary subunits to control the components connected. All the electronic components, as well as the microprocessor board itself, are supplied by means of supply (30) having supply input (31) (220 volts). The abovementioned parts are contained in the dustproof and water-tight space (1a). Also connected to the microprocessor board (29) are a keyboard (6b) and display (6a) which are situated in a space (6) which is accessible to the operator. The components in the wet section (7) are also connected to the microprocessor board. Various external equipment outside the analytical apparatus can be driven via a so-called input/output board (32), which is also connected to the processor board. In this case, that is, for example, the sampling pump. An analog output or a printer may also be used to display the analytical result and is energised in the event of an alarm (if the apparatus fails or the concentration limit is exceeded).

EXAMPLE

Figure 6:
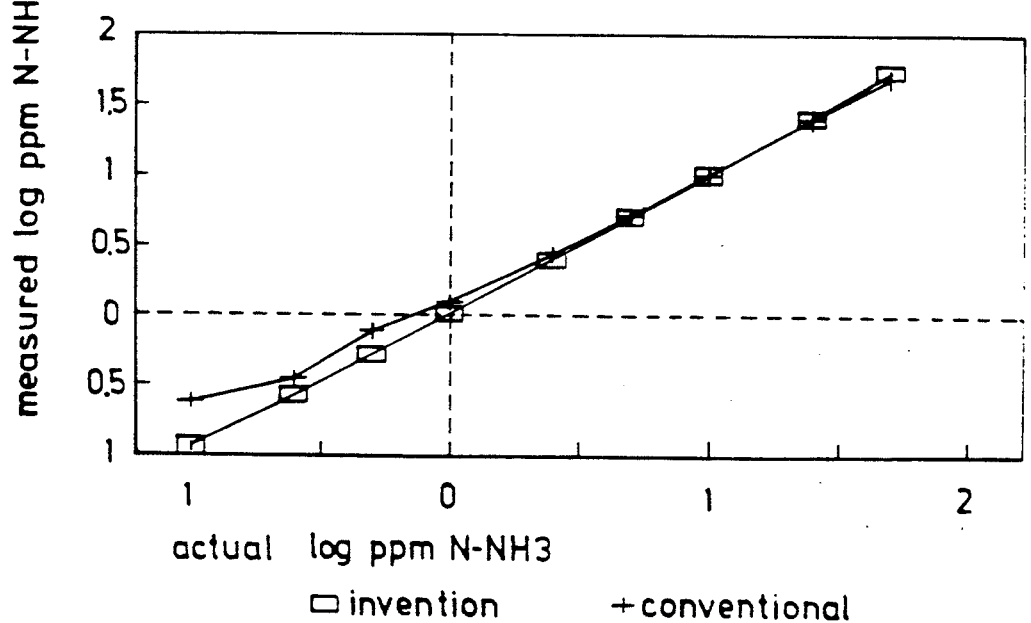
FIG. 6 is a graph showing measurements using a conventional system versus applicants new invention.

To compare the method according to the invention with a conventional method employing the standard addition method, an apparatus according to the invention was compared with a similar apparatus which operates in accordance with the conventional method. The comparison shown in FIG. 6, was performed using an ammonia analysis such as would be used in a wastewater purification plant. That is to say, a measuring range of 0 to 60 ppm N-NH$_3$, the most important part being between 2 and 5 ppm.

MEASUREMENTS

To avoid differences between the two analytical apparatuses as much as possible, they were both set up -n the same room and in the analysis, the same buffer, rinsing water, standard solution and standard samples were used. Both analytical apparatuses were provided with the same type of electrode and both with a new membrane.

A 100 ppm standard was used to determine the slope of the electrode. With the latter, the electrode vias calibrated in the measurement range from 1 to 10 ppm in the case of the apparatus of the conventional type and of 0.1 to 10 ppm in the case of the apparatus according to the invention. Measurement vias carried out with the aid of a solution prepared with ammonia and demineralised water in order to be able to compare the values obtained with the real values.

The analysis program vias carried out as follows in the two analytical apparatuses:
empty analytical vessel,
rinse analytical vessel,
wait 30 sec with electrode in solution,
rinse analytical vessel,
introduce 10 ml of sample,
add 1 ml of buffer,
wait until the electrode is stable,
measure the first potential,
add standard,
wait until the electrode is stable,
measure second potential,
calculate concentration on the basis of the potential difference.

A waiting time of 2 minutes and an added volume of 1 ml was employed in the program of the conventional apparatus. In the method according to the invention, these parameters were not set separately. The 30 sec waiting time before the analysis is performed is used to bring about conditioning of the electrode, which reduces effects due to previous measurements, if present.

A temperature correction was applied in both analytical apparatuses by measuring the temperature of the solution with a probe. In the conventional apparatuses, this is done at the end of each run, while it is done for every measurement in the apparatus according to the invention.

The accuracy and the correctness of the analysis of the standard samples were measured. 20 observations were made in each case; observations which had a large deviation at the beginning of a measurement cycle (starting-up phenomena), were not included in the calculation. The correctness has also been determined on the basis of a regression coefficient. For this purpose, the measured values are plotted against the theoretical values. In an ideal situation, a regression coefficient and an X coefficient of 1 would have to be found. The error in the X coefficient also indicates the accuracy of the measurements.

The analysis time of the conventional apparatus is approximately six minutes while that of the apparatus according to the invention is approximately 4.5 minutes.

|  | Regression Output: |
|---|---|
| New AD12013 | |
| Constant | 0.019020 |
| Estimated standard error of Y | 0.020383 |
| R squared | 0.999558 |
| Number of measurements | 9 |
| Degrees of freedom | 7 |
| X coefficient(s) | 0.988825 |
| Standard error of coefficient | 0.007852 |
| Conventional AD12015 | |
| Constant | 0.134378 |
| Estimated standard error of Y | 0.066224 |
| R squared | 0.994141 |
| Number of measurements | 9 |
| Degrees of freedom | 7 |
| X coefficient(s) | 0.879328 |
| Standard error of coefficient | 0.025513 |

| ppm N actual | ppm N | % | sd | sd % |
|---|---|---|---|---|
| *Analytical standards 2013* | | | | |
| 0 | 0.023 | error | 0.002 | 8.7 |
| 0.1 | 0.116 | 116 | 0.002 | 1.7 |
| 0.25 | 0.263 | 105 | 0.003 | 1.1 |
| 0.5 | 0.514 | 103 | 0.003 | 0.6 |
| 1 | 1.02 | 102 | 0.009 | 0.9 |
| 2.5 | 2.46 | 98 | 0.013 | 0.5 |
| 5 | 4.98 | 100 | 0.015 | 0.3 |
| 10 | 9.97 | 100 | 0.044 | 0.4 |
| 25 | 25.59 | 102 | 0.14 | 0.5 |
| 50 | 53.24 | 105 | 0.33 | 0.6 |
| *AD12015* | | | | |
| 0 | 0.209 | error | 0.02 | 9.6 |
| 0.1 | 0.237 | 237 | 0.014 | 5.9 |
| 0.25 | 0.344 | 138 | 0.006 | 1.7 |
| 0.5 | 0.76 | 152 | 0.009 | 1.2 |
| 1 | 1.23 | 123 | 0.014 | 1.1 |
| 2.5 | 2.7 | 108 | 0.011 | 0.4 |
| 5 | 5.12 | 102 | 0.015 | 0.3 |
| 10 | 9.89 | 99 | 0.035 | 0.4 |
| 25 | 24.78 | 99 | 0.09 | 0.4 |
| 50 | 49.1 | 98 | 0.6 | 1.2 |

I claim:
1. Method of determining, with the aid of an ion-selective electrode ion selective electrode the concentration of a substance to be determined, which comprises taking a known volume of a sample, a buffer is added to a sample solution in order to produce a medium in which a potential of the ion selective electrode is directly related to the concentration of a respective ion and, after a set reaction time, an initial potential of the electrode pair including an ion-selective electrode and reference electrode is measured, then a known volume of a solution having an accurately known concentration of the substance to be determined which is a standard solution is added and a change in potential produced is measured, and the concentration of the substance to be determined is calculated therefrom, including the steps of providing that the addition of the standard solution to a reaction mixture is carried out in steps, the first addition being a small one which brings about a change in potential which indicates what the concentration of a substance to be determined is approximately, then further additions are made on the basis of the change in potential produced until a final change in potential is such that it corresponds to an increase in concentration of 1.5 to 10 times the concentration of the substance to be determined which was present in the sample.

2. Method according to claim 1, wherein the electrode system is calibrated by introducing a known volume of a blank into the reaction cell and adding a known volume of buffer solution and then adding the standard solution stepwise, the added quantities of standard solution being fractions of the blank volume, and the slopes of the relationship between the potential of the electrode pair and the logarithm of the concentration is calculated from the changes in potential produced for each of the measurement ranges resulting from the additions and, at the same time, the response time of the electrode pair is also determined in each measurement range.

3. Method according to claim 1 wherein a first small quantity of standard solution is added for the purpose of indicating the concentration in the sample of the substance to be determined, which does not exceed 10 times the minimum concentration encountered in said sample or of the diluted sample.

4. Method according to claim 3, wherein, the first small quantity of standard solution is added for the purpose of indicating the concentration in the sample of the substance to be determined, which does not exceed 3 times the minimum concentration encountered in said sample or of the diluted sample.

5. Method according to claim 1 wherein a known volume of a sample is diluted to bring it within the detection range of the ion selective electrode, and wherein further additions are made on the basis of the change in potential produced until the final change in potential is such that it corresponds to an increase in concentration of 1.5 to 10 times the concentration of the substance to be determined which was present in the diluted sample.

6. Method according to claim 1, wherein in the additions of the standard solution to determine the concentration of substance in the sample, a final change in potential is aimed at which corresponds to an increase in concentration of 3 to 5 times the concentration of the substance to be determined which was present in the sample or the diluted sample.

7. Method according to claim 2, wherein a number of added quantities of standard solution with which the various measurement ranges are calibrated is chosen in such a way that more and smaller ranges are obtained in that section of the response characteristic of the ion selective electrode where it is nonlinear.

8. Method according to claim 1, wherein the minimum concentration of substance to be determined is always added to the sample by means of the standard solution in order to eliminate the inertia of the electrode system at low concentrations and to allow for this quantity in the calculation.

9. Method according to claim 1, wherein the potential of the ion selective electrode is corrected for an effect of temperature with a temperature sensor.

10. Method according to claim 1, wherein after each standard solution addition, there is not always a delay until the potential of the ion selective electrode has reached a stable signal, but the final potential is estimated on the basis of the initial potential change after a fresh addition.

11. Method according to claim 10, wherein estimation is carried out on the basis of a response time of the ion selective electrode which is determined during the calibration of the ion selective electrode in each calibration range.

12. Method according to claim 1, wherein after the last addition of standard solution, the determination of the ion selective electrode potential is delayed until it satisfies a certain drift criterion.

13. Method according to claim 2, wherein the fractions of the blank volume of standard solution are added to the blank volume in such a way that the change in concentration is not less than 1.5 times the previous concentration and not larger than 10 times said concentration, with the exception of the first addition.

* * * * *